(12) United States Patent
Amtmann (10) Patent No.: US 8,435,966 B2
(45) Date of Patent: May 7, 2013

(54) ASSOCIATIONS OF XANTHOGENATES AND CYCLODEXTRINS, AND THEIR USE

(75) Inventor: Eberhard Amtmann, Heidelberg (DE)

(73) Assignee: Biosphings AG, Frankfurt (DE)

( * ) Notice: Subject to any disclaimer, the term of this patent is extended or adjusted under 35 U.S.C. 154(b) by 497 days.

(21) Appl. No.: 12/294,740

(22) PCT Filed: Mar. 13, 2007

(86) PCT No.: PCT/EP2007/002170
§ 371 (c)(1),
(2), (4) Date: Oct. 28, 2008

(87) PCT Pub. No.: WO2007/112828
PCT Pub. Date: Oct. 11, 2007

(65) Prior Publication Data
US 2010/0240606 A1    Sep. 23, 2010

(30) Foreign Application Priority Data
Mar. 29, 2006 (DE) .................. 10 2006 014 390

(51) Int. Cl.
*A01N 43/04* (2006.01)
*A61K 31/715* (2006.01)

(52) U.S. Cl.
USPC ........................................................ 514/58

(58) Field of Classification Search ............ 514/58
See application file for complete search history.

(56) References Cited

U.S. PATENT DOCUMENTS

| 4,602,037 A | 7/1986 | Scherm et al. |
| 4,851,435 A | 7/1989 | Sauer et al. |

FOREIGN PATENT DOCUMENTS

| DE | 31 46 772 A1 | 9/1982 |
| DE | 36 25 948 A1 | 2/1987 |
| EP | 1 514 877 A1 | 3/2005 |
| JP | 57-118557 A | 7/1982 |
| JP | 62-059223 A | 3/1987 |
| JP | 2002-348276 A | 12/2002 |
| WO | WO 9614841 A1 * | 5/1996 |
| WO | WO 2004/005353 A1 | 1/2004 |
| WO | WO 2004018043 A1 * | 3/2004 |

OTHER PUBLICATIONS

Zhou et al. The Journal of Pharmacology and experimental therapeutics 2001; 298(1): 103-9, abstract only.*
Gonzalez-Roura et al. Lipids. Apr. 2002; 37(4): 401-6, abstract only.*
PubMed Health, Autoimmune disorders, May 3, 2009.*
Merck Manuals Online, Autoimmune Disorders, Sep. 2008.*
Bai et al. JPET Fast Forward, Feb. 11, 2004.*
Del Valle. Process Biochemistry 39 (2004) 1033-1046.*
Loftsson et al. Journal of Pharmaceutical Sciences, vol. 85, No. 10, Oct. 1996, pp. 1017-1025.*
Internet definition of "namely," downloaded Nov. 14, 2011.*

E. Amtmann et al., "Antitumoral activity of a sulphur-containing platinum complex with an acidic pH optimum", Cancer Chemother Pharmacol (2001), vol. 47, pp. 461-466.
W. Friebolin et al., "Synthesis and Structure-Activity Relationship of Novel Antitumoral Platinum Xanthate Complexes", J. Med. Chem. (2004), vol. 47, pp. 2256-2263.
E. Amtmann et al., "Synergistic Antiviral Effect of Xanthates and Ionic Detergents", Biochemical Pharmacology (1987), vol. 36, No. 9, pp. 1545-1549.
H.M. Abdul et al., "Protection against amyloid beta-peptide (1-42)-induced loss of phospholipid asymmetry in synaptosomal membranes by tricyclodecan-9-xanthate (D609) and ferulic acid ethyl ester: implications for Alzheimer's disease", Biochimica et Biophysica Acta (2005), vol. 1741, pp. 140-148.
G. Joshi et al., "In vivo protection of synaptosomes from oxidative stress mediated by Fe2+/H2O2 or 2,2-azobis-(2-amidinopropane) dihydrochloride by the glutathione mimetic tricyclodecan-9-yl-xanthate", Free Radical Biology & medicine (2005), vol. 38, pp. 1023-1031.
R. Sultana et al., "Protective Effect of the Xanthate, D609, on Alzheimer's Amyloid β-peptide (1-42)-induced Oxidative Stress in Primary Neuronal Cells", Free Radical Research (2004), vol. 38, No. 5, pp. 449-458.
D.C. Hooper et al., "Prevention of experimental allergic encephalomyelitis by targeting nitric oxide and peroxynitrite: Implications for the treatment of multiple sclerosis", Proc. Natl. Acad. Sci. (1997), vol. 94, pp. 2528-2533.
Z.F. Yu et al., "Pivotal Role for Acidic Sphingomyelinase in Cerebral Ischemia-Induced Ceramide and Cytokine Production, and Neuronal Apoptosis", Journal of Molecular Neuroscience (2000), vol. 15, pp. 85-97.

(Continued)

*Primary Examiner* — Layla Bland
(74) *Attorney, Agent, or Firm* — Paul D. Strain, Esq.; Strain & Strain PLLC (57) ABSTRACT

The invention is related to association products of xanthates and cyclodextrins, pharmaceutical formulations made therefrom, and medicaments containing these formulations for treating Alzheimer's, viral, tumor, cardiovascular, and autoimmune diseases such as rheumatism, multiple sclerosis, alopecia areata, lupus erythematosus, stroke, lung edema, or for use as radio-protectors. The association products contain a xanthate of general formula I

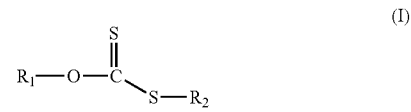

(I)

whereby $R_1$ represents a possibly substituted aryl or alkyl residue and $R_2$ represents a metal atom, a possibly substituted alkyl, alkoxy, amino or ammonium group or halogen, and a cyclodextrin, whereby the cyclodextrin can be either a substituted or non-substituted alpha-, beta- or gamma-cyclodextrin. Furthermore, the invention is related to the use of the association products for chemical syntheses.

48 Claims, 3 Drawing Sheets

OTHER PUBLICATIONS

R. Göggel et al., "PAF-mediated pulmonary edema: a new role for acid sphingomyelinase and ceramide", Nature Medicine (2004), vol. 10, No. 2, pp. 155-160.

Kazunobu Harano, et al., *[3,3]-Sigmatropic Rearrangement of Allylic Xanthates in β-Cyclodextrin Complexes*, Tetrahedron Letters, 1991, vol. 32, No. 51, pp. 7557-7558, Pergamon Press plc, Great Britain.

Masashi Eto, et al., *Molecular Orbital Studies on Pericyclic Reactions on Cinnamyl Xanthates in β-Cyclodextrin Cavities*, Chemical and Pharmaceutical Bulletin, 2000, vol. 48, No. 11, pp. 1652-1659, Pharmaceutical Society of Japan, Tokyo, Japan.

Masashi Eto et al., *Simple Synthesis of Furfuryl Sulfides Via Extrusion of COS From the Xanthates and Its Mechanistic Aspects*, Journal of the Chemical Society, Perkin Transactions 2, 1995, pp. 1155-1163.

Wolfgang Friebolin et al., "Antitumoral Activity of Non-Plantinum Xanthate Complexes", J. Med. Chem., vol. 48, No. 25 (2005), pp. 7925-7931.

Gerhard Sauer et al., "DNA and RNA virus species are inhibited by xanthates, a class of antiviral compounds with unique properties", Proc. Natl. Acad. Sci, vol. 81 (1984), pp. 3263-3267.

Eberhard Amtmann et al., "Selective Killing of Tumor Cells by Xanthates", Cancer Letters, vol. 35 (1987), pp. 237-244.

English translation of Japanese Office Action, Application No. 2009-501891, Jul. 24, 2012, 2 pgs.

Loftsson et al., "Cyclodextrin complexation of NSAIDs: physicochemical characteristics", European Journal of Pharmaceutical Sciences, vol. 1 (1993), pp. 95-101.

Canadian Office Action, Application No. 2,646,714, Jan. 4, 2013, 3 pgs.

English translation of Japanese Office Action, Appl. No, 2009-501891, Dec. 4, 2012, 3 pgs.

\* cited by examiner

Figure 1

1: HP-beta Cyclodextrin MS 0.8 D609/Cyclodextrin 1:20
2: HP-beta Cyclodextrin MS 0.8 D609/Cyclodextrin 1:10
3: HP-beta Cyclodextrin MS 1.0 D609/Cyclodextrin 1:10
4: HP-beta Cyclodextrin MS 0.6 D609/Cyclodextrin 1:10
5: Methyl-beta Cyclodextrin MS 14 D609/Cyclodextrin 1:10
6: D 609 in water
7: 9 mg/ml D 609 + 10 decomposition product

ASSOCIATIONS OF XANTHOGENATES AND CYCLODEXTRINS, AND THEIR USE

The invention is related to association products of xanthates and their use. The association products can be used for chemical syntheses and the production of pharmaceutical formulations. The formulations are suitable as medicaments. The invention is also related to the use of the medicaments containing these formulations for treating Alzheimer's, viral, tumor, cardiovascular, and autoimmune diseases such as rheumatism, multiple sclerosis, alopecia areata, lupus erythematosus, stroke, lung edema, or for use as radio-protectors.

Complex compounds of xanthates and metals, such as platinum, gold, copper, nickel, rhodium, ruthenium, bismuth, and palladium, are suitable for treating diseases, in particular tumor diseases:

"Antitumoral activity of a sulphur-containing platinum complex with an acidic pH optimum." Amtmann E, Zoller M, Wesch H, Schilling G. Cancer Chemother Pharmacol. 2001 June; 47(6):461-6.

"Synthesis and structure-activity relationship of novel antitumoral platinum xanthate complexes." Friebolin W., Schilling G., Zoller M., Amtmann E., J. Med. Chem. 2004 Apr. 22; 47(9):2256-63.

"Antitumoral activity of non-platinum xanthate complexes." Friebolin W, Schilling G, Zoller M, Amtmann E. J Med. Chem. 2005 Dec. 15; 48(25):7925-31.

Xanthates, in particular tricyclodecan-9-yl-xanthate (D609), are known to be substances with antiviral and antitumoral activity, e.g. from "DNA and RNA virus species are inhibited by xanthates, a class of antiviral compounds with unique properties" Sauer G., Amtmann E., Melber K., Knapp A., Muller K., Hummel K., Scherm A., Proc. Natl. Acad. Sci. USA, 1984 June; 81(11): 3263-7; "Selective killing of tumor cells by xanthates" by Amtmann E., Sauer G., Cancer Lett. 1987 June; 35(3): 237-44, and U.S. Pat. No. 4,602,037.

However, according to "Synergistic antiviral effect of xanthates and ionic detergents" Amtmann E., Muller-Decker K., Hoss A., Schalasta G., Doppler C., Sauer G., Biochem. Pharmacol. 1987 May 1; 36(9): 1545-9, the antiviral properties of xanthates are evident only in acidified medium or in the presence of ionic detergents.

The protective properties of D 609 in models of Alzheimer's disease have been described in "Protection against amyloid beta-peptide (1-42)-induced loss of phospholipid asymmetry in synaptosomal membranes by tricyclodecan-9-xanthate (D609) and ferulic acid ethyl ester: implications for Alzheimer's disease." by Mohmmad Abdul H., Butterfield D A., Biochim. Biophys. Acta. 2005 Jun. 30; 1741(1-2):140-8; "In vivo protection of synaptosomes from oxidative stress mediated by Fe2+/H2O2 or 2,2-azobis-(2-amidinopropane) dihydrochloride by the glutathione mimetic tricyclodecan-9-yl-xanthate." Joshi G, Sultana R, Perluigi M, Allan Butterfield D. Free Radic Biol Med. 2005 Apr. 15; 38(8):1023-31, and "Protective effect of the xanthate, D609, on Alzheimer's amyloid beta-peptide (1-42)-induced oxidative stress in primary neuronal cells." Sultana R, Newman S, Mohmmad-Abdul H, Keller J N, Butterfield D A. Free Radic Res. 2004 May; 38(5):449-58.

A protective effect of D 609 in a multiple sclerosis model is described in: "Prevention of experimental allergic encephalomyelitis by targeting nitric oxide and peroxynitrite: implications for the treatment of multiple sclerosis." Hooper D C., Bagasra O., Marini J. C., Zborek A., Ohnishi S. T., Kean R., Champion J. M., Sarker A. B., Bobroski L., Farber J. L., Akaike T., Maeda H., Koprowski H., Proc. Natl. Acad. Sci. USA. 1997 Mar. 18; 94(6):2528-33.

D 609 showed protective effect in an animal model of stroke according to "Pivotal role for acidic sphingomyelinase in cerebral ischemia-induced ceramide and cytokine production, and neuronal apoptosis." Yu Z. F., Nikolova-Karakashian M., Zhou D., Cheng G., Schuchman E. H., Mattson M. P., J. Mol. Neurosci. 2000 October; 15(2):85-97.

The protection from lung edemas by D 609 was evidenced in "PAF-mediated pulmonary edema: a new role for acid sphingomyelinase and ceramide." Goggel R., Winoto-Morbach S., Vielhaber G., Imai Y., Lindner K., Brade L., Brade H., Ehlers S., Slutsky A. S., Schutze S., Gulbins E., Uhlig S., Nat. Med. 2004 February; 10(2):155-60.

Since xanthates are chemically very labile, their pharmaceutical use in aqueous formulations, and in particular in systemic application, is not practicable for stability reasons.

Moreover, xanthates can be used in chemical synthesis only to a limited degree due to their low stability.

Xanthates such as D 609 also show pronounced irritating and hemolytic properties. For this reason, systemic application, in particular intravenous application, has been strongly limited.

We surprisingly found that association products including certain cyclodextrines can strongly improve the stability of xanthates in the presence of water. It also became evident that the hemolytic properties and toxicity of certain xanthates after intravenous application was reduced, which was surprising.

Accordingly, the association products according to the invention surprisingly provide a solution to the problem of instability of xanthates in the presence of water. Moreover, the pharmaceutical tolerability is clearly improved and systemic application is made possible.

The present invention therefore solves the problem mentioned above in that an association product and/or a pharmaceutical formulation containing a xanthate and a cyclodextrin is provided that ensures, optionally, but not exclusively, the stability of the xanthate in the presence of water. The formulation can optionally contain an adjuvant that increases the activity of the xanthate and/or an emulsifier that reduces the irritating effect of the xanthate and of the activity-increasing adjuvant.

The formulation contains an association product of cyclodextrin and a xanthate of general formula I

I whereby $R_1$ represents a optionally substituted aryl or alkyl residue.

Preferably, $R_1$ represents an adamantyl, norbornyl, tricyclodecyl, benzyl, linear or branched $C_1$-$C_{20}$ alkyl, $C_3$-$C_{20}$ cycloalkyl, furyl, pyridyl, anthracyl, naphthyl, phenanthryl, perinaphthyl or quinuclidinyl residue, and the above-mentioned linear or branched $C_1$-$C_{20}$ alkyl residue can be substituted with a hydroxyl, a $C_1$-$C_4$ alkoxy group, a halogen atom or an amino group, and the above-mentioned $C_3$-$C_{20}$ cycloalkyl residue can be substituted with a hydroxyl, a $C_1$-$C_4$ alkoxy or $C_1$-$C_4$ alkyl group, a halogen atom or an amino group. In as far as the specified compounds can exist as multiple stereoisomers, enantiomers and/or tautomers, the present invention is related to all stereoisomers, enantiomers and/or tautomers.

It is particularly advantageous for $R_1$ to be cyclododecyl, dodecyl, undecyl, decyl, tricyclo[5,2,1,0$^{2,6}$]-decyl, nonyl, octyl, bicyclo[2,2,1]-heptyl, cyclohexyl, hexyl, pentyl, butyl, propyl, isopropyl, ethyl, methyl, and toluoyl residues. A tricyclo[5,2,1,0$^{2,6}$]-decyl residue, in particular the exo/exo stereoisomer, is even more particularly advantageous.

$R_2$ represents a metal atom, a possibly substituted alkyl, alkoxy, amino or ammonium group or halogen. $R_2$ preferably represents a mono- or multi-valent metal atom, a linear $C_1$-$C_6$ alkyl residue, a hydroxy-substituted $C_1$-$C_6$ alkyl residue, a $C_1$-$C_6$ alkoxy residue, an amino group, a $C_1$-$C_6$ alkamino residue, a ($C_1$-$C_6$ alkyl)$_2$-amino residue, a ($C_1$-$C_6$ alkyl)$_3$-ammonium residue, a halogen, 2,3-dihydroxypropyl or hydroxy-($C_1$-$C_6$ alkoxy)-methyl. Sodium and potassium salts and dimethylglycyl- and methyl-esters are particularly advantageous.

Xanthate prodrugs, in which, e.g., $R_2$ is a group that can be cleaved off, are suitable. Prodrugs are converted to the active ingredient after being absorbed inside the body, usually by enzymatic reactions. Suitable cleavable $R_2$ groups are, in particular, residues with ester groups, such as e.g. —C—O—CO—R', whereby R' represents a $C_1$-$C_{10}$ alkyl residue. Particularly preferred as R' residues are methyl, ethyl, propyl, butyl, and pentyl, in particular methyl, ethyl, i-propyl, n-propyl, n-butyl, i-butyl, t-butyl.

Cyclodextrins are rings of α-1-4-linked glucose molecules that are generated during bacterial degradation of starch. The 6-, 7- or 8-membered rings, designated α-, β- and γ-cyclodextrin, can be substituted in numerous ways. According to the invention, both the non-substituted and the substituted cyclodextrins are suitable both alone and in combination of two or more.

Particularly preferred are: alpha-cyclodextrin (CAS #: 10016-20-3), alpha-cyclodextrin phosphate sodium salt (CAS #: 199684-60-1), alpha-cyclodextrin, sulfated sodium salt hydrate (CAS #: 699020-02-5), hexakis(2,3,6-tri-O-acetyl)-alpha-cyclodextrin, hexakis(2,3,6-tri-O-methyl)-alpha-cyclodextrin, hexakis(2,3,6-tri-O-octyl)-alpha-cyclodextrin (CAS #: 140395-31-9), hexakis-6-bromo-6-deoxy-alpha-cyclodextrin (CAS #: 53784-82-0), hexakis-6-iodo-6-deoxy-alpha-cyclodextrin (CAS #: 131105-41-4), hexakis(6-O-tertbutyldimethylsilyl)-alpha-cyclodextrin, butylalpha-cyclodextrin, succinyl-alpha-cyclodextrin, (2-hydroxypropyl)-alpha-cyclodextrin (CAS #: 128446-33-3), beta-cyclodextrin (CAS #: 7585-39-9), beta-cyclodextrin hydrate (CAS #: 68168-23-0), beta-cyclodextrin phosphate sodium salt (CAS #: 199684-61-2), beta-cyclodextrin sulfate, beta-cyclodextrin, sulfated sodium salt (CAS #: 37191-69-8), hydroxypropyl-beta-cyclodextrin (CAS #: 94035-02-6), 6-monodeoxy-6-monoamino-beta-cyclodextrin, 6-O-alpha-D-glucosyl-beta-cyclodextrin (CAS #: 92517-02-7), 6-O-alpha-maltosyl-beta-cyclodextrin hydrate (CAS #: 104723-60-6), heptakis-6-azido-6-deoxy-beta-cyclodextrin, heptakis(2,3-di-O-acetyl-6-O-sulfo)-beta-cyclodextrin heptasodium salt (CAS #: 196398-66-0), heptakis-(2,3-di-O-methyl6-O-sulfo)-beta-cyclodextrin heptasodium salt (CAS #: 201346-23-8), heptakis(2,6-di-O-methyl)-beta-cyclodextrin (CAS #: 51166-71-3), heptakis-(2,6-di-O-ethyl)-beta-cyclodextrin (CAS #: 111689-03-3), heptakis(2,3,6-tri-O-methyl)-beta-cyclodextrin (CAS #: 55216-11-0), heptakis(2,3,6-tri-O-acetyl)-beta-cyclodextrin, heptakis-(2,3,6-tri-O-benzoyl)-beta-cyclodextrin (CAS #: 23666-43-5), heptakis-(2,3,6-tri-O-ethyl)-beta-cyclodextrin (CAS #: 111689-01-1), heptakis-6-iodo-6-deoxy-beta-cyclodextrin (CAS #: 30754-23-5), heptakis-6-(dimethyl-tert-butylsilyl)-6-deoxy-beta-cyclodextrin, heptakis-6-bromo-6-deoxy-beta-cyclodextrin, monoacetyl-beta-cyclodextrin, diacetyl-beta-cyclodextrin, triacetyl-beta-cyclodextrin (CAS #: 23739-88-0), heptakis(3-O-acetyl-2,6-di-O-methyl)-beta-cyclodextrin (CAS #: 131889-29-7), heptakis-(6-O-maltosyl)-beta-cyclodextrin, heptakis(6-O-sulfo)-beta-cyclodextrin heptasodium salt (CAS #: 197587-31-8), heptakis(6-O-t-butyldimethylsilyl-2,3-di-O-acetyl)-beta-cyclodextrin, succinyl-(2-hydroxypropyl)-beta-cyclodextrin, (2,6-di-O-)ethyl-beta-cyclodextrin, (2-carboxyethyl)-beta-cyclodextrin, (2-hydroxyethyl)-beta-cyclodextrin (CAS #: 128446-32-2), (2-hydroxypropyl)-beta-cyclodextrin (CAS #: 128446-35-5), butyl-beta-cyclodextrin, methyl-beta-cyclodextrin (CAS #: 128446-36-6), silyl((6-O-tert-butyldimethyl)-2,3,-di-O-acetyl)-beta-cyclodextrin, succinyl-beta-cyclodextrin, gamma-cyclodextrin (CAS #: 17465-86-0), gamma-cyclodextrin hydrate (CAS #: 91464-90-3), gamma-cyclodextrin phosphate sodium salt (CAS #: 199684-62-3), sulfopropyl-beta-cyclodextrin, carboxymethyl-gamma-cyclodextrin, octakis(2,3,6-tri-O-acetyl)-gamma-cyclodextrin, octakis(2,3,6-tri-O-methyl)-gamma-cyclodextrin, octakis(2,6-di-O-pentyl)-gamma-cyclodextrin, octakis-6-(dimethyl-tert-butylsilyl)-6-deoxy-gamma-cyclodextrin, octakis-6-bromo-6-deoxy-gamma-cyclodextrin (CAS #: 53784-84-2), octakis-6-iodo-6-deoxy-gamma-cyclodextrin (CAS #: 168296-33-1), octakis(6-O-t-butyldimethylsilyl)-gamma-cyclodextrin, succinyl-gamma-cyclodextrin, (2-hydroxypropyl)-gamma-cyclodextrin (CAS #: 128446-34-4), acetyl-gamma-cyclodextrin, butyl-gamma-cyclodextrin and mixtures of two or more of the specified cyclodextrins.

Even more particularly well-suited are beta-cyclodextrins and, in particular, hydroxypropyl-beta-cyclodextrin and methyl-beta-cyclodextrin.

The activity-increasing adjuvant preferably is an ionic detergent. It can be a fatty acid with 6-19 C atoms or salt thereof. Particularly advantageous are the potassium salts of decanoic, undecanoic or lauric acid. The activity-increasing adjuvant can also be a sulfate with an aliphatic residue of 8-18 C atoms. Na-lauric acid sulfate is particularly preferred. Other options for the adjuvant are deoxycholic acid or a pharmaceutically tolerable salt thereof or a phosphonic acid.

Formulations containing 0.1 to 10 parts of activity-increasing adjuvant per one part of xanthate have proven to be well-suited. Particularly advantageous is a ratio of xanthate to activity-increasing adjuvant of 1:1.

Preferably, the irritating effect-reducing emulsifier is a steroid. Cholesterol, cholestanol, cholanic acid, chondrillasterol, and α, β, γ sisterol are suitable. Cholesterol is particularly advantageous. Also suitable as irritating effect-reducing emulsifier are phospholipids, in particular phosphatidylcholine, phosphatidylserine, phosphatidylinositol or stearylamine.

A formulation, in which the irritating effect-reducing emulsifier is cholesterol, the activity-increasing adjuvant is the Na or K salt of decanoic acid, the cyclodextrin is hydroxypropyl-beta-Cyclodextrin or methyl-beta-cyclodextrin, and the xanthate is tricyclo[5,2,1,0$^{2,6}$]-9yl-xanthate, is particularly preferred. In particular, there is one part potassium salt of decanoic acid, 4 parts cholesterol, and 3-20 parts cyclodextrin per one part xanthate.

Another particularly preferred formulation contains tricyclo[5,2,1,0$^{2,6}$]-9yl-xanthate and methyl-beta-cyclodextrin or hydroxypropyl-beta-cyclodextrin, whereby there preferably are 3-20 parts cyclodextrin per one part xanthate.

Furthermore, the present invention provides medicaments for treating Alzheimer's, viral, tumor, cardiovascular, and autoimmune diseases such as rheumatism, multiple sclerosis, alopecia areata, lupus erythematosus, stroke, lung edema, or for use as radioprotectors. These agents can just as well contain the pharmaceutically active xanthate in the form of a prodrug. In addition, the agents contain common excipients. Other active ingredients can also be contained therein, provided they adversely affect neither the effect nor the stability of the xanthates.

The agents can be provided in the form of dry substances, lyophilized products, solutions, suspensions, emulsions, ointments, creams, lotions or sprays. Preferred forms of administration are, e.g., tablets, tinctures, solutions for injection, lotions, sprays, juices, and in particular ointments, whereby a lipophilic substance or any other suitable non-aqueous or aqueous formulation base can be used as the base of the ointment.

The pharmaceutical formulations and agents according to the invention are suitable for treating Alzheimer's, viral, tumor, cardiovascular, and autoimmune diseases such as rheumatism, multiple sclerosis, alopecia areata, lupus erythematosus, stroke, lung edema, or for use as radioprotectors.

In addition, the cyclodextrin-xanthate association products according to the invention can be used in chemical syntheses. Accordingly, for example for the production of xanthate compounds, in particular of metal complexes, the xanthate can be made to associate either with soluble or solid carrier-bound cyclodextrins. The cyclodextrin-xanthate association products are suitable, in particular, for producing metal complexes of the general formula X—Z—Y, whereby both X and Y as well as X only or Y only represent a xanthate residue. X and Y can be the same or different. Z represents a metal that is capable of forming complexes with xanthates, such as platinum, copper, gold, nickel, rhodium, ruthenium, bismuth, and palladium. The production of asymmetrical complexes (X unequal to Y) can be effected by serial reaction of carrier material-bound cyclodextrin with a xanthate, followed by a metal, followed by another xanthate or any other molecule capable of forming a metal complex, such as, e.g., dithiocarbamate, an amine or diamine.

The following examples illustrate the invention in more detail without limiting it. Unless specified otherwise, all part- and %-specifications in the present invention are by weight.

EXAMPLE 1

Stabilization of Various Xanthates by Methyl-Beta-Cyclodextrin at 60° C.

Solutions each containing 10 mg/ml methylxanthate, propylxanthate, butylxanthate, heptyixanthate, hexylxanthate, decylxanthate, isopropylxanthate, or tricyclo[5,2,1,0$^{2,6}$]-decylxanthate (D 609) in water were incubated for 24 h at 60° C. either in the presence or absence of 100 mg/ml methyl-beta-cyclodextrin. Xanthates decompose in aqueous medium into the corresponding alcohol, $CS_2$, and, depending on the type of xanthate salt, KOH or NaOH. The decomposition of xanthates can therefore be detected quantitatively by measuring the pH value and using calibration curves. The results of the measurements are summarized in Table 1. In all cases, there was significantly less decomposition in the presence of cyclodextrin.

TABLE 1

| Xanthate | % Decomposition − Cyclodextrin | % Decomposition + Cyclodextrin | Stabilization factor |
|---|---|---|---|
| Methyl | 50 | 1 | 50 |
| Ethyl | 10 | 1 | 10 |
| Propyl | 20 | 2 | 10 |
| Butyl | 20 | 1 | 20 |
| Pentyl | 20 | 1 | 20 |
| Hexyl | 20 | 1 | 20 |
| Decyl | 10 | 1 | 10 |
| Isopropyl | 20 | 1 | 20 |
| D 609 | 20 | 1 | 20 |

EXAMPLE 2

Stabilization of Exo/Exo D 609 by Hydroxypropyl-Beta-Cyclodextrin at Room Temperature Solutions containing 10 mg/ml exo/exo D 609 in water were incubated at room temperature either in the presence or absence of 100 mg/ml methyl-beta-cyclodextrin. The xanthate, D 609, decomposes in aqueous solutions to form the tricyclodecanol, $CS_2$, and KOH. The decomposition of D 609 can therefore be detected quantitatively by measuring the pH value and using calibration curves. The pH value of the individual solutions was determined after 45 days using PAN-PEHA strips (Schleicher & Schüll). The solution containing D 609 in pure water had a pH value of 12.5. This corresponds to complete decomposition. The pH value of the solution containing cyclodextrin was measured to be 7.0. This corresponds to <0.1% decomposition. Accordingly, the rate of decomposition is at least 1000-fold lower in the presence of cyclodextrin.

EXAMPLE 3

Stabilization Effect of Different Cyclodextrins on D 609 at 60° C.

Figure 1:
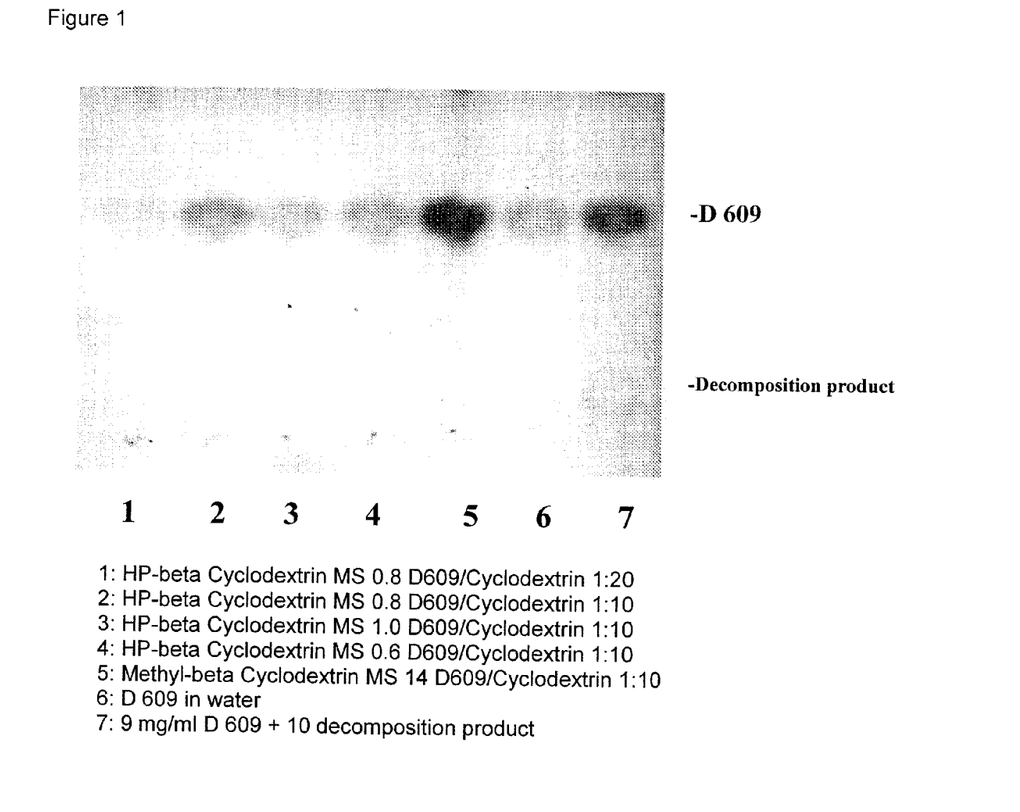

Exo/exo D 609 was dissolved in solutions (100 mg/ml) containing various cyclodextrins (10 mg/ml). The samples were incubated for eight days at 60° C. 10 μl of each sample were diluted with 90 μl of water and 100 μl ethylacetate/3 mg/ml p-bromoacetophenone were added. After shaking for 30 minutes, 5 μl of the ethylacetate phase each were applied to a RP-18 thin layer plate and the plate was placed for 15 minutes in a TLC chamber containing acetonitrile as mobile phase. A freshly prepared solution of 9 mg/ml D 609 plus 1 mg/ml of a D 609 solution that had been incubated at 95° C. for 48 h (decomposition control) was used as calibration sample. The D 609-specific spots were visualized under UV light and photographed. As is evident from FIG. 1, the various cyclodextrins show different protective effects from decomposition. Methyl-beta-cyclodextrin works the best by far. Amongst the hydroxypropyl-beta-cyclodextrins, HP-beta-cyclodextrin with a substitution rate of MS 0.8 was the most effective.

EXAMPLE 4

Reduction of the Toxicity of D 609 after Intravenous Application by Cylodextrin

The exo/exo isomer of D 609 or hexylxanthate were dissolved in 0.9% NaCl or 0.9% NaCl/30% hydroxy-beta-cyclodextrin at a concentration of 30 mg/ml. Subsequently, dilutions were prepared using 0.9% NaCl solution to obtain concentrations of 30, 20, 10, and 5 mg/ml D 609 or hexylxanthate. Three female Balb C mice each received injections of 0.2 ml/20 g body weight of each solutions into the lateral tail vein. The animals were monitored for 48 h after injection and survival was recorded. The results are shown in Table 2.

TABLE 2

| Dose [mg/kg] | Animals receiving injections/surviving animals | | | |
|---|---|---|---|---|
| | D 609 control | D 609 + cyclodextrin | Hexylxanthate control | Hexylxanthate + cyclodextrin |
| 300 | 3/0 | 3/0 | 3/0 | 3/0 |
| 200 | 3/0 | 3/3 | 3/0 | 3/0 |
| 100 | 3/0 | 3/3 | 3/2 | 3/2 |
| 50 | 3/3 | 3/3 | 3/3 | 3/3 |

The number of surviving animals is clearly increased by cyclodextrin at the higher D 609-doses. The LD50 for D 609 alone was found to be 75 mg/kg, whereas the LD50 in the presence of cyclodextrin was 250 mg/kg. The LD50 of hexylxanthate was 130 mg/kg both in the presence and absence of cyclodextrin.

EXAMPLE 5

Inhibition of the Hemolytic Effect of Xanthates

Figure 2:
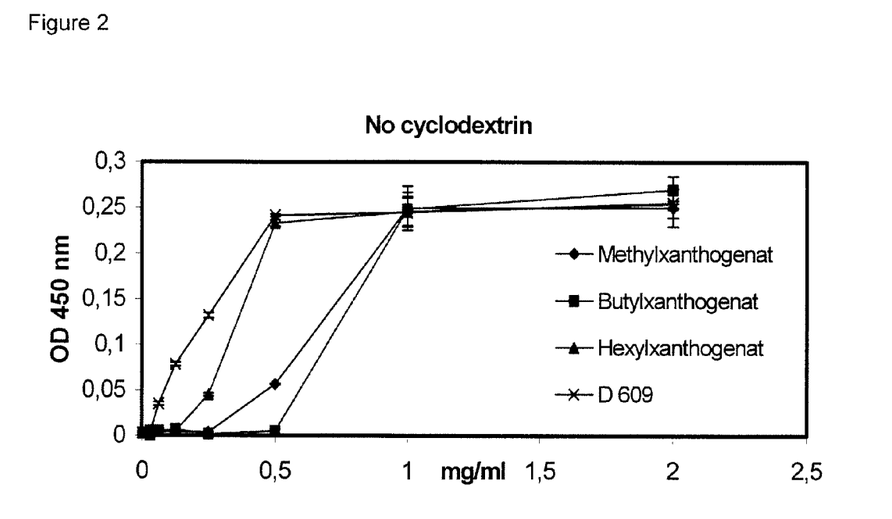
Figure 3:
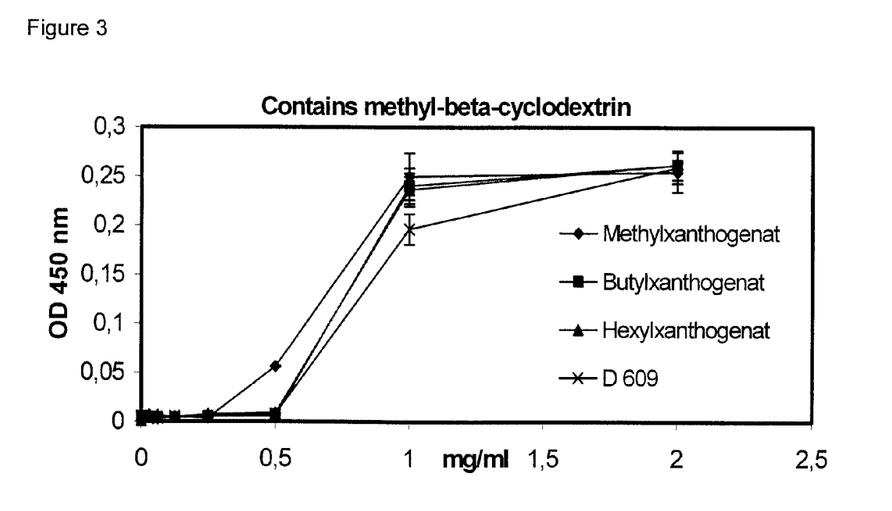

Venous blood was taken from female Balb C mice by retroorbital puncture and heparin was added to the blood. The blood was then diluted 1:75 using phosphate-buffered saline. Methyl-, butyl, and hexylxanthate as well as exo/exo D 609 were dissolved in phosphate-buffered saline (stock solution 10 mg/ml). 100 µl diluted blood and 100 µl diluted xanthate solution each were placed in 96-well microtiter plates to obtain final concentrations of 2, 1, 0.5, 0.25, 0.125, 0.063, and 0.031 mg/ml of xanthate. Saline served as the control. After incubation at room temperature for 30 minutes, a centrifugation at 5,000 g for 5 min was performed and the supernatants were removed. The absorption of the supernatants at 450 nm (OD 450) was measured using an ELISA-Reader. Dose-response curves (FIGS. 2 and 3) were used to determine the concentrations at which 50% of the maximal absorption was reached and at which, therefore, 50% of the erythrocytes were lysed (IC50). The dose-response curves for the presence and absence of cyclodextrin show no significant differences for methyl- and butylxanthate. In contrast, the hemolytic effect of hexylxanthate and D 609 was reduced strongly in the presence of cyclodextrin. Complete hemolysis was achieved with 1 mg/ml methyl- and butylxanthate both in the presence and in the absence of cyclodextrin. Hexylxanthate and D 609 alone were completely hemolytic at concentrations of 0.5 mg/ml each. In the presence of cyclodextrin, this effect was present only at 1.0 and 2.0 mg/ml, respectively. 50% hemolysis (IC50) in the absence of cyclodextrin was found for 0.6 mg/ml methyl-, 0.8 mg/ml butyl-, 0.3 mg/ml hexylxanthate, and 0.125 mg/ml D 609. The corresponding values found in the presence of cyclodextrin were 0.65, 0.65, 0.75, and 0.8 mg/ml, respectively. Accordingly, there was no influence on the hemolytic effect of methyl- and butylxanthate. In contrast, a clear increase of the IC50 by a factor of 2.5 and 6.4 was found for hexylxanthate and D 609, respectively.

EXAMPLE 6

Antiviral Efficacy of Association Products of Beta-Hydroxycyclodextrin and D609

Human lung carcinoma cells (Calu-6) in D-MEM medium (supplemented with 10% fetal calf serum) were seeded in 24-well plates (Greiner) (3×106 cells/plate each). After incubation for 24 h at 37° C. in a 5% $CO_2$ atmosphere, the medium was decanted and 0.1 ml viral suspension (HSV-1, strain Angelotti, 200 plaque-forming units/ml) were added. After incubation at 37° C. for one hour, fresh medium (DMEM, 10% serum, 0.85 g $NaHCO_3$/l) containing D609 (exo/exo isomer) or a mixture of D609 and beta-hydroxypropyl-cyclodextrin (b-HP) (Sigma, Munich, No 33, 260-7) was added.

Figure 4:
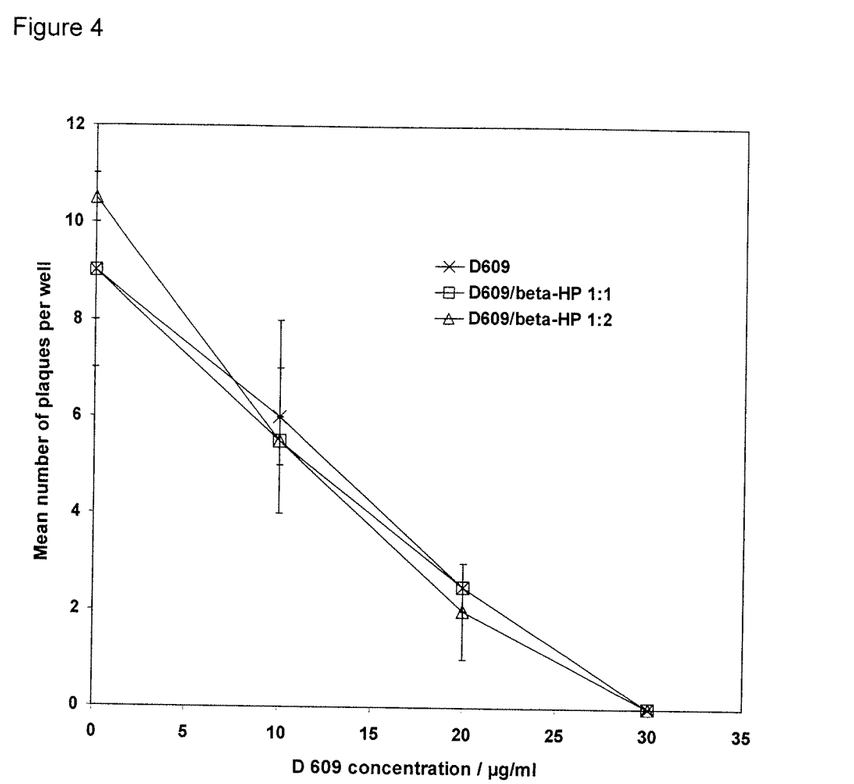

The following concentrations were set-up:
D609:0, 10, 20, 30 µg/ml.
D609/b-HP, 1:1:0, 10/10, 20/20, 30/30 µg/ml
D609/b-HP, 1:2:0, 10/20, 20/40, 30/60 µg/ml After 72 h, the medium was decanted and the plates were fixed with 3% formalin and stained with 0.5% crystal violet. After the plates were dried, the number of plaques per well was determined and the means±standard deviation were calculated. The results (dose-response curves) are plotted in FIG. 4. The dose-response curves of D609/b-HP, 1:1 and D609/b-HP, 1:2 do not differ significantly from the dose-response curve of D609 alone. Accordingly, the addition of beta-hydroxypropyl-cyclodextrin has no influence on the antiviral activity of D609.

EXAMPLE 7

Preparation of a Cream 5 g exo/exo D609, 50 g hydroxypropyl-beta-cyclodextrin, 3.5 g 1,2-propandiol, 4.5 g paraffin oil, 1.5 g cetyl-dimethicon copolyol, 0.5 g trihydroxystearate, and purified water up to 100 g were mixed and homogenized using a cylinder mill or similar device. The cream is suitable for topical application.

EXAMPLE 8

Preparation of a Solution for Injection 100 mg exo/exo D609, 1 g hydroxypropyl-beta-cyclodextrin, and 90 mg NaCl were mixed and purified water was added to adjust the final volume to 10 ml. The solution for injection is ready for use and can be stored for extended periods of time without any problems.

EXAMPLE 7

Preparation of a Capsule

50 mg exo/exo D609 and 500 mg methyl-beta-cyclodextrin were mixed and filled into a hard-gelatin capsule coated to be gastric juice-resistant. The capsules are suitable for oral application.

EXAMPLE 8

Preparation of a Tablet 36 mg exo/exo D609, 364 mg hydroxypropyl-beta-cyclodextrin, 200 mg micro-crystalline cellulose, 20 mg carboxymethyl-starch Na type A, and 30 mg talcum were mixed and compacted to form tablets. Subsequently, the tablet is coated with a gastric juice-resistant film-forming agent. The tablets are suitable for oral application.

The invention claimed is:
1. Pharmaceutical formulation containing association products containing a xanthate of formula I

(I)

whereby $R_1$ represents an adamantyl, norbornyl, tricyclodecyl, benzyl, linear or branched $C_1$-$C_{20}$ alkyl, $C_3$-$C_{20}$ cycloalkyl, furyl, pyridyl, anthracyl, naphthyl, phenanthryl, perinaphthyl or quinuclidinyl residue, and the above-mentioned linear or branched $C_1$-$C_{20}$ alkyl residue can be substituted with a hydroxyl, a $C_1$-$C_4$ alkoxy group, a halogen atom or an amino group, and the above-mentioned $C_3$-$C_{20}$ cycloalkyl residue can be substituted with a hydroxyl, a $C_1$-$C_4$ alkoxy or $C_1$-$C_4$ alkyl group, a halogen atom or an amino group and $R_2$ represents a metal atom other than a metal atom selected from the group consisting of platinum, gold, copper, nickel, rhodium, ruthenium, bismuth, and palladium, an unsubstituted or substituted alkyl, alkoxy, amino or ammonium group, a cleavable group comprising a substituent containing an ester group, or halogen, and a cyclodextrin.

2. Pharmaceutical formulation according to claim 1, whereby the cyclodextrin is selected from: alpha-cyclodextrin (CAS #: 10016-20-3), alpha-cyclodextrin phosphate sodium salt (CAS #: 199684-60-1), alpha-cyclodextrin, sulfated sodium salt hydrate (CAS #: 699020-02-5), hexakis(2,3,6-tri-O-acetyl)-alpha-cyclodextrin, hexakis(2,3,6-tri-O-methyl)-alpha-cyclodextrin, hexakis(2,3,6-tri-O-octyl)-alpha-cyclodextrin (CAS #: 140395-31-9), hexakis-6-bromo-6-deoxy-alpha-cyclodextrin (CAS #: 53784-82-0), hexakis-6-iodo-6-deoxy-alpha-cyclodextrin (CAS #: 131105-41-4), hexakis(6-O-tertbutyl-dimethylsilyl)-alpha-cyclodextrin, butyl-alpha-cyclodextrin, succinyl-alpha-cyclodextrin, (2-hydroxypropyl)-alpha-cyclodextrin (CAS #: 128446-33-3), beta-cyclodextrin (CAS #: 7585-39-9), beta-cyclodextrin hydrate (CAS #: 68168-23-0), beta-cyclodextrin phosphate sodium salt (CAS #: 199684-61-2), beta-cyclodextrin sulfate, beta-cyclodextrin, sulfated sodium salt (CAS #: 37191-69-8), hydroxypropyl-beta-cyclodextrin (CAS #: 94035-02-6), 6-monodeoxy-6-monoamino-beta-cyclodextrin, 6-O-alpha-D-glucosyl-beta-cyclodextrin (CAS #: 92517-02-7), 6-O-alpha-maltosyl-beta-cyclodextrin hydrate (CAS #: 104723-60-6), heptakis-6-azido-6-deoxy-beta-cyclodextrin, heptakis(2,3-di-O-acetyl-6-O-sulfo)-beta-cyclodextrin heptasodium salt (CAS #: 196398-66-0), heptakis-(2,3-di-O-methyl-6-O-sulfo)-beta-cyclodextrin heptasodium salt (CAS #: 201346-23-8), heptakis(2,6-di-O-methyl)-beta-cyclodextrin (CAS #: 51166-71-3), heptakis-(2,6-di-O-ethyl)-beta-cyclodextrin (CAS #: 111689-03-3), heptakis(2,3,6-tri-O-methyl)-beta-cyclodextrin (CAS #: 55216-11-0), heptakis(2,3,6-tri-O-acetyl)-beta-cyclodextrin, heptakis-(2,3,6-tri-O-benzoyl)-beta-cyclodextrin (CAS #: 23666-43-5), heptakis-(2,3,6-tri-O-ethyl)-beta-cyclodextrin (CAS #: 111689-01-1), heptakis-6-iodo-6-deoxy-beta-cyclodextrin (CAS #: 30754-23-5), heptakis-6-(dimethyl-tert-butylsilyl)-6-deoxy-beta-cyclodextrin, heptakis-6-bromo-6-deoxy-beta-cyclodextrin, monoacetyl-beta-cyclodextrin, diacetyl-beta-cyclodextrin, triacetyl-beta-cyclodextrin (CAS #: 23739-88-0), heptakis(3-O-acetyl-2,6-di-O-methyl)-beta-cyclodextrin (CAS #: 131889-29-7), heptakis-(6-O-maltosyl)-beta-cyclodextrin, heptakis(6-O-sulfo)-beta-cyclodextrin heptasodium salt (CAS #: 197587-31-8), heptakis(6-O-t-butyldimethylsilyl-2,3-di-O-acetyl)-beta-cyclodextrin, succinyl-(2-hydroxypropyl)-beta-cyclodextrin, (2,6-di-O-)ethyl-beta-cyclodextrin, (2-carboxyethyl)-beta-cyclodextrin, (2-hydroxyethyl)-beta-cyclodextrin (CAS #: 128446-32-2), (2-hydroxypropyl)-beta-cyclodextrin (CAS #: 128446-35-5), butyl-beta-cyclodextrin, methyl-beta-cyclodextrin (CAS #: 128446-36-6), silyl((6-O-tert-butyldimethyl)-2,3,-di-O-acetyl)-beta-cyclodextrin, succinyl-beta-cyclodextrin, gamma-cyclodextrin (CAS #: 17465-86-0), gamma-cyclodextrin hydrate (CAS #: 91464-90-3), gamma-cyclodextrin phosphate sodium salt (CAS #: 199684-62-3), sulfopropyl-beta-cyclodextrin, carboxymethyl-gamma-cyclodextrin, octakis(2,3,6-tri-O-acetyl)-gamma-cyclodextrin, octakis(2,3,6-tri-O-methyl)-gamma-cyclodextrin, octakis(2,6-di-O-pentyl)-gamma-cyclodextrin, octakis-6-(dimethyl-tert-butylsilyl)-6-deoxy-gamma-cyclodextrin, octakis-6-bromo-6-deoxy-gamma-cyclodextrin (CAS #: 53784-84-2), octakis-6-iodo-6-deoxy-gamma-cyclodextrin (CAS #: 168296-33-1), octakis(6-O-t-butyldimethylsilyl)-gamma-cyclodextrin, succinyl-gamma-cyclodextrin, (2-hydroxypropyl)-gamma-cyclodextrin (CAS #: 128446-34-4), acetyl-gamma-cyclodextrin, butyl-gamma-cyclodextrin and mixtures thereof.

3. Pharmaceutical formulation according to claim 1, wherein it further comprises an adjuvant comprising an ionic detergent that increases the activity of the xanthate and/or an emulsifier.

4. Pharmaceutical formulation according to claim 1, wherein $R_1$ is cyclododecyl, dodecyl, undecyl, decyl, tricyclo [5,2,1,0$^{2,6}$]-decyl, nonyl, octyl, bicyclo[2,2,1]-heptyl, cyclohexyl, hexyl or toluoyl residue.

5. Pharmaceutical formulation according to claim 1, wherein $R_2$ is a cleavable group comprising a substituent containing ester group, wherein the cleavable group is a methyl ester having the formula —$CH_2$—O—CO—R', wherein R' represents a $C_1$-$C_{10}$ alkyl residue.

6. Pharmaceutical formulation according to claim 1, wherein $R_2$ is sodium or potassium.

7. Pharmaceutical formulation according to claim 3, wherein it contains an emulsifier comprising a steroid or a phospholipid.

8. Pharmaceutical formulation according to claim 7, wherein the emulsifier is cholesterol or phosphatidylcholine.

9. Pharmaceutical formulation according to claim 3, wherein it contains 1 to 10 parts of emulsifier per one part of xanthate.

10. Pharmaceutical formulation according to claim 3, wherein it contains an adjuvant and the adjuvant comprises an ionic detergent, selected from the group consisting of a fatty acid with 6 to 19 C atoms and an alkylsulfate with 8 to 18 C atoms.

11. Pharmaceutical formulation according to claim 10, wherein the adjuvant is selected from phosphonic acid, deoxycholic acid or a pharmaceutically tolerable salt thereof.

12. Pharmaceutical formulation according to claim 1, wherein it contains two or more cyclodextrins.

13. Pharmaceutical formulation according to claim 1, wherein it contains hydroxypropyl-beta-cyclodextrin (CAS #: 94035-02-6) and/or methyl-beta-cyclodextrin (CAS #: 128446-36-6).

14. A method for treating a viral or tumor disease, comprising administering to a patient having a viral or tumor disease, in an amount effective to treat said disease, a pharmaceutical formulation according to claim 1.

15. A method according to claim 14, wherein the pharmaceutical formulation is an ointment that contains the pharmaceutical formulation in a lipophilic substance.

16. A method according to claim 14, wherein the pharmaceutical formulation is an ointment that contains the pharmaceutical formulation in an aqueous ointment base.

17. A method according to claim 14, wherein the pharmaceutical formulation comprises the pharmaceutical formulation in the form of dry, mixed or single substances for dissolution.

18. Pharmaceutical formulation according to claim 3, wherein it contains hydroxypropyl-beta-cyclodextrin (CAS #: 94035-02-6) and/or methyl-beta-cyclodextrin (CAS #: 128446-36-6).

19. Pharmaceutical formulation according to claim 4, wherein $R_2$ is sodium or potassium.

20. Pharmaceutical formulation according to claim 3, wherein $R_1$ is a cyclododecyl, dodecyl, undecyl, decyl, tricyclo[5,2,1,0$^{2,6}$]-decyl, nonyl, octyl, bicyclo[2,2,1]-heptyl, cyclohexyl, hexyl or toluoyl residue.

21. Pharmaceutical formulation containing association products containing a xanthate of formula I (I)

whereby $R_1$ represents an adamantyl, norbornyl, tricyclodecyl, benzyl, linear or branched $C_1$-$C_{20}$ alkyl, $C_3$-$C_{20}$ cycloalkyl, furyl, pyridyl, anthracyl, naphthyl, phenanthryl, perinaphthyl or quinuclidinyl residue, and the above-mentioned linear or branched $C_1$-$C_{20}$ alkyl residue can be substituted with a hydroxyl, a $C_1$-$C_4$ alkoxy group, a halogen atom or an amino group, and the above-mentioned $C_3$-$C_{20}$ cycloalkyl residue can be substituted with a hydroxyl, a $C_1$-$C_4$ alkoxy or $C_1$-$C_4$ alkyl group, a halogen atom or an amino group and $R_2$ represents sodium or potassium, and a cyclodextrin.

22. Pharmaceutical formulation according to claim 21, whereby the cyclodextrin is selected from: alpha-cyclodextrin (CAS #: 10016-20-3), alpha-cyclodextrin phosphate sodium salt (CAS #: 199684-60-1), alpha-cyclodextrin, sulfated sodium salt hydrate (CAS #: 699020-02-5), hexakis(2,3,6-tri-O-acetyl)-alpha-cyclodextrin, hexakis(2,3,6-tri-O-methyl)-alpha-cyclodextrin, hexakis(2,3,6-tri-O-octyl)-alpha-cyclodextrin (CAS #: 140395-31-9), hexakis-6-bromo-6-deoxy-alpha-cyclodextrin (CAS #: 53784-82-0), hexakis-6-iodo-6-deoxy-alpha-cyclodextrin (CAS #: 131105-41-4), hexakis(6-O-tertbutyl-dimethylsilyl)-alpha-cyclo-dextrin, butyl-alpha-cyclodextrin, succinyl-alpha-cyclodextrin, (2-hydroxypropyl)-alpha-cyclodextrin (CAS #: 128446-33-3), beta-cyclodextrin (CAS #: 7585-39-9), beta-cyclodextrin hydrate (CAS #: 68168-23-0), beta-cyclodextrin phosphate sodium salt (CAS #: 199684-61-2), beta-cyclodextrin sulfate, beta-cyclodextrin, sulfated sodium salt (CAS #: 37191-69-8), hydroxypropyl-beta-cyclodextrin (CAS #: 94035-02-6), 6-monodeoxy-6-monoamino-beta-cyclodextrin, 6-O-alpha-D-glucosyl-beta-cyclodextrin (CAS #: 92517-02-7), 6-O-alpha-maltosyl-beta-cyclodextrin hydrate (CAS #: 104723-60-6), heptakis-6-azido-6-deoxy-beta-cyclodextrin, heptakis(2,3-di-O-acetyl-6-O-sulfo)-beta-cyclodextrin heptasodium salt (CAS #: 196398-66-0), heptakis-(2,3-di-O-methyl-6-O-sulfo)-beta-cyclodextrin heptasodium salt (CAS #: 201346-23-8), heptakis(2,6-di-O-methyl)-beta-cyclodextrin (CAS #: 51166-71-3), heptakis-(2,6-di-O-ethyl)-beta-cyclodextrin (CAS #: 111689-03-3), heptakis(2,3,6-tri-O-methyl)-beta-cyclo-dextrin (CAS #: 55216-11-0), heptakis(2,3,6-tri-O-acetyl)-beta-cyclodextrin, heptakis(2,3,6-tri-O-benzoyl)-beta-cyclodextrin (CAS #: 23666-43-5), heptakis-(2,3,6-tri-O-ethyl)-beta-cyclodextrin (CAS #: 111689-01-1), heptakis-6-iodo-6-deoxy-beta-cyclodextrin (CAS #: 30754-23-5), heptakis-6-(dimethyl-tert-butylsilyl)-6-deoxy-beta-cyclodextrin, heptakis-6-bromo-6-deoxy-beta-cyclodextrin, monoacetyl-beta-cyclodextrin, diacetyl-beta-cyclodextrin, triacetyl-beta-cyclodextrin (CAS #: 23739-88-0), heptakis(3-O-acetyl-2,6-di-O-methyl)-beta-cyclodextrin (CAS #: 131889-29-7), heptakis-(6-O-maltosyl)-beta-cyclodextrin, heptakis(6-O-sulfo)-beta-cyclodextrin heptasodium salt (CAS #: 197587-31-8), heptakis(6-O-t-butyldimethylsilyl-2,3-di-O-acetyl)-beta-cyclodextrin, succinyl-(2-hydroxypropyl)-beta-cyclodextrin, (2,6-di-O-)ethyl-beta-cyclodextrin, (2-carboxyethyl)-beta-cyclodextrin, (2-hydroxyethyl)-beta-cyclodextrin (CAS #: 128446-32-2), (2-hydroxypropyl)-beta-cyclodextrin (CAS #: 128446-35-5), butyl-beta-cyclodextrin, methyl-beta-cyclodextrin (CAS #: 128446-36-6), silyl((6-O-tert-butyldimethyl)-2,3,-di-O-acetyl)-beta-cyclodextrin, succinyl-beta-cyclodextrin, gamma-cyclodextrin (CAS #: 17465-86-0), gamma-cyclodextrin hydrate (CAS #: 91464-90-3), gamma-cyclodextrin phosphate sodium salt (CAS #: 199684-62-3), sulfopropyl-beta-cyclodextrin, carboxymethyl-gamma-cyclodextrin, octakis(2,3,6-tri-O-acetyl)-gamma-cyclodextrin, octakis(2,3,6-tri-O-methyl)-gamma-cyclodextrin, octakis(2,6-di-O-pentyl)-gamma-cyclodextrin, octakis-6-(dimethyl-tert-butylsilyl)-6-deoxy-gamma-cyclodextrin, octakis-6-bromo-6-deoxy-gamma-cyclodextrin (CAS #: 53784-84-2), octakis-6-iodo-6-deoxy-gamma-cyclodextrin (CAS #: 168296-33-1), octakis(6-O-t-butyldimethylsilyl)-gamma-cyclodextrin, succinyl-gamma-cyclodextrin, (2-hydroxypropyl)-gamma-cyclodextrin (CAS #: 128446-34-4), acetyl-gamma-cyclodextrin, butyl-gamma-cyclodextrin and mixtures thereof.

23. Pharmaceutical formulation according to claim 21, further comprising an adjuvant comprising an ionic detergent that increases the activity of the xanthate and/or an emulsifier.

24. Pharmaceutical formulation according to claim 21, wherein $R_1$ is a cyclododecyl, dodecyl, undecyl, decyl, tricyclo[5,2,1,0$^{2,6}$]-decyl, nonyl, octyl, bicyclo[2,2,1]-heptyl, cyclohexyl, hexyl or toluoyl residue.

25. Pharmaceutical formulation according to claim 23, wherein it contains an emulsifier and the emulsifier is a steroid or a phospholipid.

26. Pharmaceutical formulation according to claim 23, wherein it contains 1 to 10 parts of emulsifier per one part of xanthate.

27. Pharmaceutical formulation according to claim 23, wherein it contains an adjuvant and the adjuvant is a fatty acid with 6 to 19 C atoms or an alkylsulfate with 8 to 18 C atoms.

28. Pharmaceutical formulation according to claim 27, wherein the adjuvant is selected from phosphonic acid, deoxycholic acid and a pharmaceutically tolerable salt thereof.

29. Pharmaceutical formulation according to claim 21, wherein it contains two or more cyclodextrins.

30. Pharmaceutical formulation according to claim 21, wherein it contains hydroxypropyl-beta-cyclodextrin (CAS #: 94035-02-6) and/or methyl-beta-cyclodextrin (CAS #: 128446-36-6).

31. Pharmaceutical formulation according to claim 23, wherein $R_1$ is a cyclododecyl, dodecyl, undecyl, decyl, tricyclo[5,2,1,0$^{2,6}$]-decyl, nonyl, octyl, bicyclo[2,2,1]-heptyl, cyclohexyl, hexyl or toluoyl residue.

32. Pharmaceutical formulation according to claim 24, wherein $R_2$ is sodium or potassium.

33. Pharmaceutical formulation according to claim 23, wherein it contains hydroxypropyl-beta-cyclodextrin (CAS #: 94035-02-6) and/or methyl-beta-cyclodextrin (CAS #: 128446-36-6).

34. A method for treating a viral or tumor disease, comprising administering to a patient having a viral or tumor disease, in an amount effective to treat said disease, a pharmaceutical formulation according to claim 21.

35. A method according to claim 34, wherein the pharmaceutical formulation is an ointment that contains the pharmaceutical formulation in a lipophilic substance.

36. A method according to claim 34, wherein the pharmaceutical formulation is an ointment that contains the pharmaceutical formulation in an aqueous ointment base.

37. A method according to claim 34, wherein the pharmaceutical formulation comprises the pharmaceutical formulation in the form of dry, mixed or single substances for dissolution.

38. Pharmaceutical formulation according to claim 1, wherein the cyclodextrin comprises a beta-cyclodextrine.

39. Pharmaceutical formulation according to claim 3, wherein the cyclodextrin comprises a beta-cyclodextrine.

40. Pharmaceutical formulation according to claim 23, wherein the cyclodextrin comprises a beta-cyclodextrine.

41. Pharmaceutical formulation according to claim 1, wherein $R_2$ is a cleavable group comprising a substitutent containing ester group, wherein the cleavable group is a methyl ester.

42. A method for treating a viral or tumor disease, comprising administering to a patient having a viral or tumor disease, in an amount effective to treat said disease, a pharmaceutical formulation according to claim 13.

43. Pharmaceutical formulation according to claim 1, wherein the cyclodextrin comprises an alpha-cyclodextrine.

44. Pharmaceutical formulation according to claim 3, wherein the cyclodextrin comprises a alpha-cyclodextrine.

45. Pharmaceutical formulation according to claim 23, wherein the cyclodextrin comprises a alpha-cyclodextrine.

46. Pharmaceutical formulation according to claim 1, wherein the cyclodextrin comprises a gamma-cyclodextrine.

47. Pharmaceutical formulation according to claim 3, wherein the cyclodextrin comprises a gamma-cyclodextrine.

48. Pharmaceutical formulation according to claim 23, wherein the cyclodextrin comprises a gamma-cyclodextrine.

* * * * *